United States Patent [19]
Blount et al.

[11] Patent Number: 5,926,024
[45] Date of Patent: Jul. 20, 1999

[54] SYSTEM AND METHOD FOR MEASURING FLUID PROPERTIES BY FORMING A COAXIAL TRANSMISSION LINE IN A CASED WELL

[75] Inventors: Curtis G. Blount, Wasilla, Ak.; James K. Eastlack, Plano, Tex.; Michael D. Erwin, Anchorage, Ak.

[73] Assignee: Atlantic Richfield Company, Los Angeles, Calif.

[21] Appl. No.: 08/368,610

[22] Filed: Jan. 4, 1995

[51] Int. Cl.$^6$ ........................................................ G01V 3/18
[52] U.S. Cl. ........................ 324/324; 73/61.43; 324/640
[58] Field of Search ........................... 324/324, 633–637, 324/639, 640–643, 332, 333–335; 73/61.41, 61.43, 61.44

[56] References Cited

U.S. PATENT DOCUMENTS

| | | | |
|---|---|---|---|
| 2,785,374 | 3/1957 | Fay et al. | 324/324 |
| 3,279,249 | 10/1966 | Tocanne | 324/324 |
| 4,429,273 | 1/1984 | Mazzagatti | 324/664 |
| 4,774,680 | 9/1988 | Agar | 324/698 |
| 4,862,060 | 8/1989 | Scott et al. | 324/639 |
| 4,996,490 | 2/1991 | Scott et al. | 324/639 |
| 5,025,222 | 6/1991 | Scott et al. | 324/639 |
| 5,103,181 | 4/1992 | Gaisford et al. | 324/637 |
| 5,157,339 | 10/1992 | Scott et al. | 324/640 |
| 5,263,363 | 11/1993 | Agar | 73/61.44 |

FOREIGN PATENT DOCUMENTS

| | | | |
|---|---|---|---|
| B67911 | 6/1992 | Australia | 324/324 |
| 1139369 | 1/1983 | Canada | 324/324 |

*Primary Examiner*—Walter E. Snow
*Assistant Examiner*—Jay M. Patidar
*Attorney, Agent, or Firm*—Drude Faulconer

[57] ABSTRACT

Apparatus for insertion in a well which is producing fluids from multiple zones for measuring the concentration of water in the fluids flowing through the well to determine which zone may be producing excessive quantities of water. The apparatus transmits microwave frequency range radiation within a section of the wellbore. The apparatus may utilize a portion of the well casing and a conductor member which is centered in the wellbore by spaced apart centralizers to form a coaxial transmission line within the wellbore. The apparatus may be traversed through the wellbore on a wireline type cable for continuous measurement of the water content of the water-oil mixture flowing through the well to determine which zone is producing excessive amounts of water into the production fluids. A change in operating frequency of an oscillator furnishing the microwave range energy is compared with power loss through the apparatus to determine if a water-in-oil or oil-in-water emulsion is present in the wellbore fluid flow stream. Alternate embodiments of the apparatus include downhole transmitting and receiving antennas for directing an RF energy beam through the wellbore fluids. A volumetric flowmeter is connected to the apparatus for continuous measurement of fluid flow rate for comparison with the water concentration in the well fluids at various points in the wellbore.

15 Claims, 6 Drawing Sheets

SYSTEM AND METHOD FOR MEASURING FLUID PROPERTIES BY FORMING A COAXIAL TRANSMISSION LINE IN A CASED WELL

FIELD OF THE INVENTION

The present invention pertains to a method and apparatus for determining the composition of wellbore fluids within a well wherein the apparatus measures the alteration of microwave energy characteristics as a function of the water and gas content of the fluids.

BACKGROUND

In the production of oil and gas from subterranean wells, the composition of fluids entering the wellbore from the formation zone or zones being produced may include a substantial amount of water and/or gas mixed with crude oil. For example, certain wells are configured to produce crude oil from multiple formation zones spaced along the wellbore and the water content of the fluid mixture flowing into the well from one zone may be greater than from one or more other zones which are also producing into the well. Relatively mature oil fields which are being subjected to waterflooding may produce a substantial amount of water into a production well from one zone while an oil-water mixture having a much lower water content is being produced into the same well from another zone. Accordingly, it is desirable to be able to identify the zone which is producing an unwanted quantity of water so that certain treatment operations may be carried out to reduce such water flow. Moreover, it may also be desirable to be able to measure the water content of the fluid mixture flowing from a well to the surface to eliminate expensive fluid separation equipment and associated flow measuring devices at the wellhead.

Several systems have been developed for aboveground installations for measuring the composition of a mixture of water and oil, such as is typically produced from many hydrocarbon-producing wells. U.S. Pat. No. 4,429,273, issued Jan. 31, 1984 to R. P. Mazzagatti describes an oil-water monitor characterized by an electrical co-axial transmission line having a signal source of electromagnetic radiation in the form of a continuous wave signal with a frequency preferably of 100 kilohertz to 500 megahertz. U.S. Pat. Nos. 4,774,680 and 5,263,363 to J. Agar disclose oil-water monitors which measure energy absorption properties of an oil-water mixture in the oil continuous phase or water continuous phase. U.S. Pat. Nos. 4,862,060; 4,996,490 and 5,157,339 to Scott et al. and assigned to the assignee of the present invention, describe apparatus for measuring the concentration of water in crude oil, for example, wherein a radio frequency (RF) range signal generator, preferably operating in a microwave frequency range, is provided in the form of an unbuffered oscillator which is connected to a device through which the fluid mixture flows and forms part of a coaxial microwave transmission line. The devices described in the Scott et al. patents are all adapted for use interposed in a process flow line at the surface and not for downhole operations or measurements.

U.S. Pat. No. 5,025,222 to Scott et al. describes further applications for the above-mentioned type of fluid measurement apparatus. Still further, U.S. Pat. No. 5,103,181 to Gaisford et al. describes a method and system for measuring the properties of fluid mixtures utilizing the complex dielectric properties of these mixtures flowing through a pipe which acts as a waveguide for propagating radio frequency electromagnetic energy.

None of the above-mentioned systems or devices are adapted for "downhole" measurement of fluids flowing within a well. Certain devices have been proposed for measuring the composition of fluids downhole but these devices lack the accuracy desired for many well fluid measurement applications and they do not measure more than a small portion of the total fluid flow through the well. Moreover, these prior art devices are typically interposed in a reduced diameter conduit which is connected to a seal-forming device such as an inflatable packer. Such devices restrict the flow of fluids through the wellbore, are difficult to insert and retrieve, and cannot be continuously moved through the wellbore to monitor changes in the flow conditions and fluid compositions at any selected position in the wellbore.

Accordingly, there has been a continuing and increasing need to develop a system wherein a measurement device can be placed in a well, traversed through the well without significantly impeding fluid-flow within the well and be capable of more accurately measuring the composition of the wellbore fluids at substantially any selected position in the wellbore and while measuring substantially the entire fluid flowstream in the well. In particular, there has been a need to provide a method and system for accurately measuring the so-called watercut or percentage of water in the total fluid flow stream flowing through a well so that, in particular, for wells which are producing fluids from multiple spaced-apart zones, those zones which are producing excessive quantities of water can be identified and isolated from producing into the well, if desired. It is to these ends that the present invention has been developed.

SUMMARY OF THE INVENTION

The present invention provides a unique system and apparatus for measuring the composition of wellbore fluids, in situ or downhole. In particular, a system is provided for measuring the water content of a fluid production flowing through a well at selected positions along the wellbore so that earth formation zones which may be producing excessive water into the well can be identified with a high degree of accuracy. The system is operable to accurately measure the water content of the fluid mixture regardless of whether the fluid is in a water continuous phase or oil continuous phase.

In accordance with another important aspect of the invention, a system is provided for accurately measuring the composition of wellbore fluids at selected points in a wellbore, which system does not substantially impede the flow of fluid through the wellbore. The system is operable to measure the water content, in particular, of a crude oil-water mixture, compensate for any gas in the mixture and also measure the total flow rate of fluids flowing through the well at the composition measurement points.

The system includes an apparatus which advantageously utilizes the well casing as an outer conductor for a section of coaxial transmission line formed by the apparatus wherein radio frequency range (preferably microwave frequency) electromagnetic energy is propagated within the well at the measurement point. The apparatus is insertable in the well and comprises a center conductor, preferably sheathed with a dielectric covering operable to prevent short circuiting of the microwave energy transmission path. An oscillator circuit is coupled to the apparatus at the surface or downhole and is driven by a free-running voltage controlled oscillator. A signal receiver monitors the change in frequency caused by impedance pulling of the oscillator due to the change in the dielectric constant of the fluid mixture flowing through the wellbore. Incident and reflected or transmitted RF power is measured to determine whether an oil-in-water or water-in-oil emulsion is present at the measurement point. Alternate embodiments of the invention measure RF signal strength or intensity within the wellbore to determine fluid composition.

The present invention also provides an improved method for measuring wellbore fluids, in situ, and, particularly, the composition of fluids at selected points in a wellbore which is producing fluids from multiple spaced-apart earth formation zones. The inventive method contemplates identifying subterranean fluid-producing zones which are producing an excessive amount of water so that such water production can be curtailed or eliminated through adjustment of reservoir injection procedures or by blocking off casing perforations, for example, through which excessive water content fluids are flowing.

Those skilled in the art will further appreciate the above-described advantages and features of the invention together with other superior aspects thereof upon reading the detailed description which follows in conjunction with the drawing.

DESCRIPTION OF PREFERRED EMBODIMENTS

In the description which follows like elements are marked through the specification and drawing with the same reference numerals, respectively. The drawing figures are not necessarily to scale and certain features are shown in schematic or somewhat generalized form in the interest of clarity and conciseness.

Figure 1:
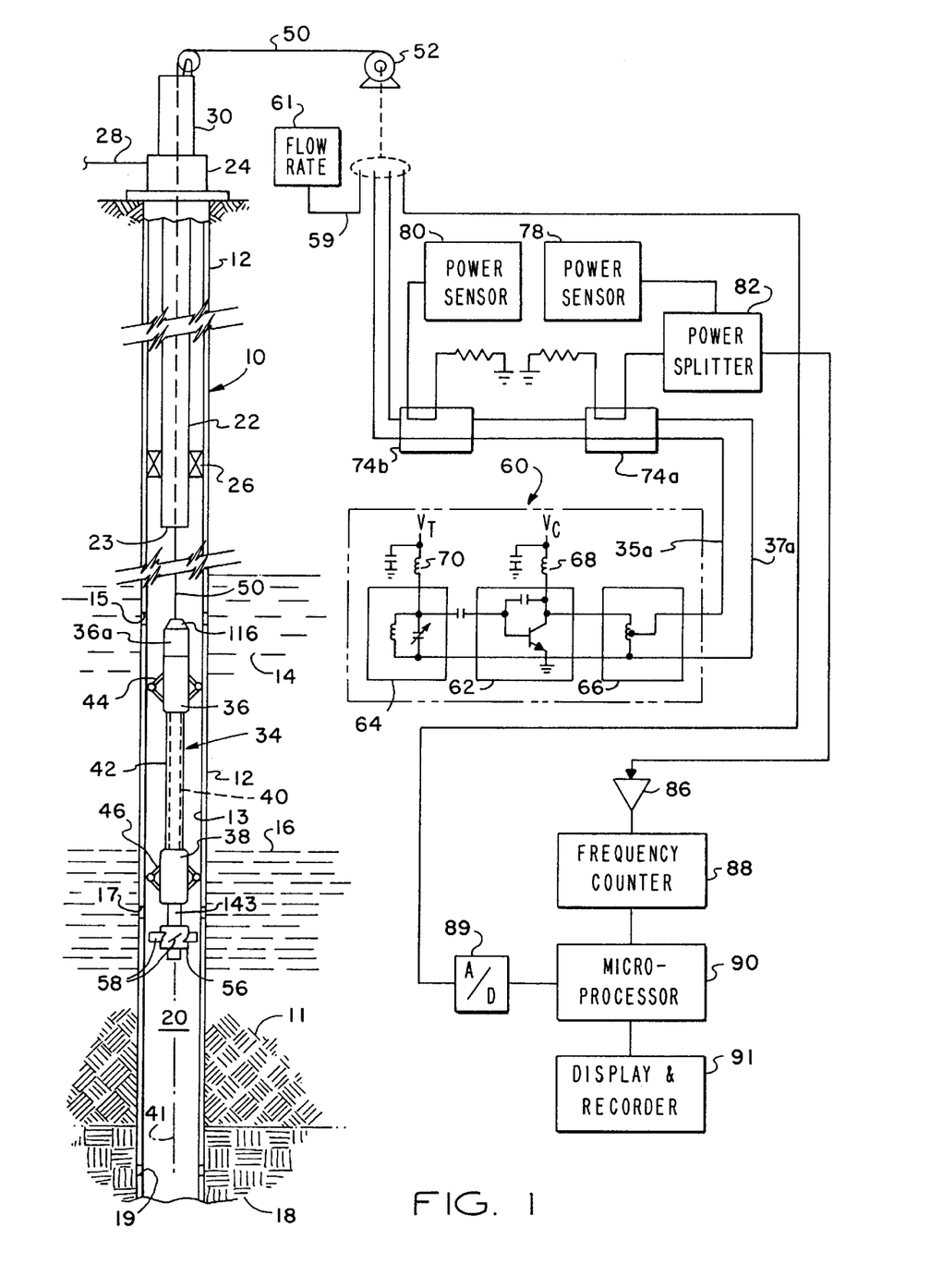
FIG. 1 is a schematic diagram of a fluid production well showing one preferred embodiment of the system of the present invention.

Referring to FIG. 1, there is illustrated a typical hydrocarbon fluid production well, generally designated by the numeral 10, having a conventional cylindrical steel casing 12 extending within an earth formation 11 and through multiple formation zones 14, 16 and 18, for example. Each of the zones 14, 16 and 18 is in communication with a wellbore space 20 by way of respective sets of casing perforations 15, 17 and 19. A production tubing string 22 depends within the casing 12 from a wellhead 24. A conventional packer 26 delimits the wellbore space 20 whereby fluids being produced into the wellbore 20 through the respective sets of perforations 15, 17 and 19 flow through the production tubing 22 to the wellhead 24 and then through a suitable flowline 28. A conventional wireline lubricator 30 is shown disposed on the wellhead 24 for use in conjunction with the present invention.

As a result of the injection of an oil production stimulating or drive fluid, such as water, the water content of oil flowing into the wellbore space 20 from one or more of the zones 14, 16 and 18 may be excessive. Moreover, water already in place in one or more of the formation zones 14, 16 and 18 may, depending on the particular well, tend to be produced into the well in an excessive amount. In particular, wells penetrating mature oilfields may produce a water-oil mixture from one or more production zones wherein the water content is as high as ninety to ninety-five percent of the total fluid flow. The economics of production and the processing equipment for separating water from oil, downstream of the flow line 28, may in some instances be such that a total water content of the flow stream of, say ninety-two percent is tolerable, whereas once the water content reaches ninety-six or ninety-eight percent, certain operations must be performed on the well to reduce the water content in the produced fluid stream.

Accordingly, relatively sensitive composition measurements of fluid flowing within the well 10 are desired to be made so that production from one or more of the formation zones 14, 16 and 18 may be curtailed by reducing water injection or by inserting certain devices within the well to close off one or more sets of the casing perforations 15, 17 or 19, for example. Those skilled in the art will appreciate that determining the source of excessive water flowing into the wellbore space 20, for example, has been difficult using known methods and equipment, particularly if a well is simultaneously producing from two or more spaced apart production zones.

The present invention provides a system and method for accurately measuring the composition of fluids within the wellbore itself to determine, in particular, the amount of water in a crude oil production flow stream. In providing a method and system for measuring the composition and flow rate of wellbore fluids at selected points within a well, consideration must be given to providing apparatus which may be inserted into the wellbore through a production tubing string which is normally of a diameter significantly less than the diameter of the well casing or wellbore space through which the fluid to be measured is flowing. Moreover, it is also desirable to provide an apparatus which is insertable in a well for measuring fluid composition and flow rate at selected points which does not significantly impede fluid flow and may be easily traversed along the wellbore to make measurements at several selected points or to make substantially continuous measurements as the apparatus is being traversed through the wellbore.

U.S. Pat. Nos. 4,862,060; 4,996,490 and 5,157,339 to Scott et al. describe a device for measuring the concentration of one liquid in another, particularly relatively low and high concentrations of water in crude oil. The apparatus described in these patents is characterized by an unbuffered or unisolated free-running oscillator circuit which is connected to a fluid measurement section having a coaxial transmission path for electromagnetic radiation in the microwave frequency range. The so-called measurement section of the apparatus includes a conduit section having a center conductor extending therethrough and wherein the conduit itself forms a part of the conductive path or circuit. The apparatus described in the above-mentioned patents is capable of detecting a change in operating frequency of the oscillator as a function of the change of the composition of the liquid mixture being conducted through the measurement section.

For relatively low concentrations of water in a water-oil mixture, the oscillator circuit of the systems mentioned above exhibits changes in operating frequency which can be easily measured and compared to a pre-established relationship between the oscillator operating frequency and the composition of the water-oil mixture to determine the water content. However, when the water content of the mixture increases to a range of about fifty percent to eighty-six percent, by volume, the mixture inverts to an oil in water emulsion and apparatus with a metal center or core conductor and a metal outer conductor/conduit in direct contact with the mixture being measured undergoes a loss in field intensity due to a short circuit between the conductor elements. Under these conditions, a coaxial transmission line of the type described in the '060 patent becomes incapable of measuring the water content of the water-oil mixture. Accordingly, as set forth in the '490 patent the inner or center conductor is provided with a sheath, preferably formed of a non-metallic material and having a low loss tangent dielectric characteristic. The provision of this insulating sheath over the center conductor as well as the apparatus and method for measuring the power loss incurred during operation thereof provides for carrying out a method wherein the concentration of oil in water or water in oil may be ascertained based on incident and reflected microwave power. The apparatus and method of the present invention utilizes the unique features of a microwave based apparatus for measuring the water content of an oil-water mixture as set forth in the above-mentioned Scott et al. patents and these patents are incorporated herein by reference.

Referring again to FIG. 1, an apparatus according to one preferred embodiment of the invention is operable to be inserted in the wellbore space 20 through the wireline lubricator 30, the wellhead 24 and the tubing string 22 in a conventional manner used for inserting downhole tools and instruments. The apparatus is illustrated in somewhat schematic form in FIG. 1 and generally designated by the numeral 34. The apparatus 34 includes two spaced apart body members 36 and 38 which are preferably of generally cylindrical form and dimensioned to be insertable through the tubing string 22 into the wellbore space 20. The body members 36 and 38 are interconnected by a generally cylindrical steel rod 40 comprising a center conductor over which is disposed a tubular insulating sheath 42. Each of the body members 36 and 38 is provided with centralizers 44 and 46, respectively, for centering the conductor 40 in the wellbore space 20 substantially coaxial with respect to the longitudinal central axis 41 of the well 10 and the cylindrical inside wall 13 of the casing 12. The centralizers 44 and 46 will be further described herein in conjunction with FIGS. 2A and 2B. The apparatus 34 is adapted to be traversed through the wellbore space 20 by a conventional wireline type flexible cable, generally designated by the numeral 50 in FIG. 1, which is operable to be extended through the wireline lubricator 30 and wound on a reversible winch drum 52 having a suitable slip ring assembly, not shown, provided therein for communicating electrical signals between the cable 50 and measurement apparatus comprising part of the system of the invention and disposed on the surface of the earth formation 11.

Referring further to FIG. 1, the apparatus 34 also preferably includes a suitable volumetric flow meter, generally designated by the numeral 56, and shown depending from the body member 38. The meter 56 may be of a type having plural circumferentially spaced turbine blades 58 which may be foldable or retractable to permit deployment of the meter 56 connected to the apparatus 34 through the tubing string 22. Once the flow meter 56 is disposed in the wellbore space 20, the blades 58 are operable to radially extend or unfold to be of sufficient length to extend substantially across the cross sectional flow area of the space 20 so that an accurate fluid flow rate measurement of fluid flowing through the space 20 may be obtained. Placement of the flow meter 56 distal of the apparatus 34 may also provide improved mixing of fluid flowing between a set of casing perforations and the distal end 23 of the tubing string 22 so that a more accurate reading of the composition of a water-oil mixture may be obtained with the apparatus 34. The flow meter 56 may be of a type commercially available and its use in measuring the flow rate within a wellbore such as the wellbore space 20 is often referred to in the art as a "spinner survey". However, disposing the flow meter 56 in the position shown with respect to the apparatus 34 may provide the above-mentioned advantage in the use of the apparatus 34. The flowmeter 56 is operable to transmit signals through suitable conductor means disposed in cable 50 and by way of conductor means 59 to a recording and/or readout unit 61, FIG. 1.

An important advantage of the present invention resides in the provision of the apparatus 34 wherein the center conductor 40 cooperates with a section of the casing 12, generally between the body members 36 and 38 to form a measurement section characterized as a coaxial transmission line. The center conductor 40 preferably comprises a generally cylindrical rod or tube member, preferably formed of a metal such as stainless steel extending between and supporting the body members 36 and 38. The sheath 42 is preferably formed of a relatively easy-to-fabricate plastic, such as polypropylene, a plastic sold under the trademark Delring or one of the fluorocarbon plastics. Alternatively, certain ceramics or similar materials may also be used for the sheath 42 as long as they are low-loss-tangent dielectric materials. The fit between the sheath 42 and the center conductor 40 is preferably a forced or line-to-line fit, although some clearance may be permitted as long as fluid flow between the center conductor and the sheath is prohibited. The ratio of the outer diameter of the sheath 42 to the outer diameter of the center conductor 40 is preferably in the range of about two to one. With the center conductor configuration of the type described herein, a circuit associated with the apparatus 34, and to be described hereinbelow, retains good field intensity and prevents short circuiting of the center conductor to the outer conductor comprising the casing 12, in an unwanted location. Accordingly, an oscillator associated with the above-mentioned circuit retains good load pulling characteristics with good resolution of phase and the interface between the sheath 42 and the fluid in the space 20 is a new propagation medium which has desirable operating characteristics.

When the apparatus 34 is operating in a liquid composition which is high in water content, a so-called water continuous phase or oil-in-water emulsion, the conductivity of the composition is high compared to a good dielectric but low compared to a good conductor 40. Accordingly, since the liquid flowing through the space 20 is in direct contact with the wall surface 13 and the center conductor, the insulating sheath 42 prevents RF electromagnetic energy from being shorted out immediately at the point where the energy enters the measurement section of the apparatus 34 or where the fluid cross sectional flow area begins with respect to the center conductor 40. Still further, the sheath 42 now becomes the primary region where the RF energy field is propagated with the conductive fluid becoming a pseudo outer wall of the measurement section. The cross sectional measurement of a water and oil mixture is still preserved due to the large skin depth of the microwave or RF energy at the operating frequency of the apparatus 34. This skin depth is large enough through the water as the conducting medium of the outer half of the coaxial transmission line formed by the measurement section. The properties of the propagated RF energy still reflect the changing content of the oil and the water and this is related through the pulling of the unisolated oscillator which is described herein below. A very thin dielectric coating on the center conductor 40 will cause a very low impedance with a liquid composition having a high water content and therefore the RF energy would be reflected at the fluid interface.

RF energy is not propagated in the interior of a good conductor. The conductor guides the electromagnetic waves. The energy travels in the region between the conductors in a coaxial transmission system with a good dielectric. The currents that are established at the conductor surfaces propagate into the conductor in a direction perpendicular to the direction of the current density. The current density or electric field intensity established at the surface of a good conductor decays rapidly looking into the conductor.

Figure 2A:
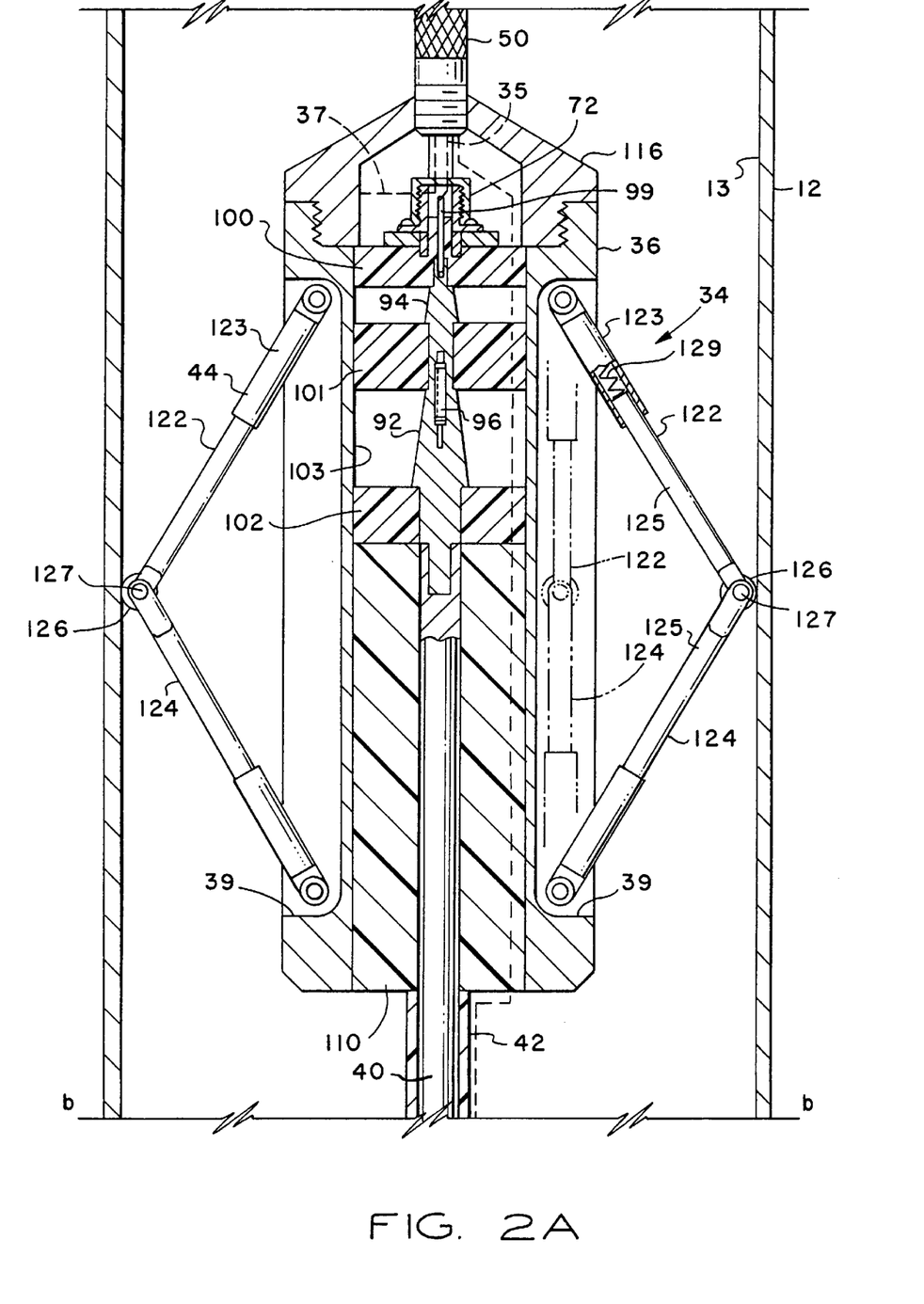
FIGS. 2A and 2B comprise a central section view showing the downhole apparatus portion of the system of FIG. 1 in a working position.

The apparatus 34 is operably connected through suitable conductor means 35 and 37, see FIG. 2A, extending within the cable 50, to a source of radio frequency range energy comprising an unbuffered or unisolated, free running isolator, generally designated by the numeral 60 in FIG. 1. The oscillator 60 includes an active circuit 62 operably connected to a tuning circuit 64 and to an impedance matching network circuit 66. The circuit 62 is adapted to receive a constant DC voltage $V_c$, from a source not shown, and by way of a filter circuit 68. The tuning circuit 64 is also adapted to receive a controllable DC voltage, $V_t$, from another source, not shown, by way of a second filter circuit 70. The oscillator 60 has an appreciable load pulling characteristic. The fundamental operating frequency of the oscillator 60 is changed as the complex load is changed on the output circuit of the oscillator. The oscillator 60 may be of a type commercially available, such as from Avantek Company, Santa Clara, Calif., as their Model VT08030, voltage controlled oscillator. By way of example, the oscillator 60 has a maximum load pulling characteristic of about 35 MHz at a nominal 200 MHz operating frequency into all phases of a short circuit at the end of a 50 ohm line stretcher (approximately 0.5 db return loss). The oscillator 60 may operate at a nominal frequency of up to 1.60 GHz.

The oscillator 60 is operably connected to the apparatus 34 through conductors 35 and 37, which may comprise a coaxial cable, and a suitable connector 72, FIG. 2A, which is in electrically conductive engagement with the center conductor 40 at the body member 36 and, at the opposite end of the center conductor, to the outer conductor or casing 12 by way of the centralizer 46. The body member 36 is also in electrical conductive engagement with the casing 12 through centralizer 44. As shown in FIG. 1, directional couplers 74a and 74b are interposed in conductors 35a and 37a extending between the oscillator 60 and the drum 52 and operably connected through the conductors 35 and 37, FIG. 2A, to the downhole apparatus 34. Also, as shown in FIG. 1, separate power sensors 78 and 80 are connected to the respective directional couplers, as shown, and are arranged to measure the incident power transmitted to the apparatus 34 and the reflected power returned from the apparatus 34. A power splitter 82 is connected in circuit with the coupler 74a and power sensor 78 for measuring the incident power transmitted to the apparatus 34. The change in operating frequency of the oscillator circuit 60 is sensed by a circuit which includes an amplifier 86, a frequency counter 88, a microprocessor 90 and a display and recorder device 91. The oscillator 60 and the circuit elements associated with and including the directional couplers 74a and 74b may be disposed on the apparatus 34 in a body extension portion 36a, for example, FIG. 1.

The operation of the apparatus 34, in conjunction with the surface disposed control circuits and components of the system described above, is carried out by sweeping the operating frequency of the oscillator 60 across a range suitable for the particular composition being measured in the wellbore space 20. A change in the operating frequency for a particular tuned frequency may be compared with the output of the oscillator 60 and corresponding to a range of percentages of oil in water or water in oil. Concomitant with the change in operating frequency, the power loss characteristic of the apparatus 34 may be measured by comparing the power sensed at the respective power sensors 78 and 80 for a particular operating frequency and by referring to the diagram of FIG. 3 of frequency versus mixture content and frequency versus power loss to determine whether, in the case of a water-oil mixture, a water-in-oil condition exists or an oil-in-water condition exists, and wherein the percentage of one in the other may be determined. The diagram of FIG. 3 may, of course, be presented in the form of a digital data base accessible by a suitable computer or other recording means.

Figure 2B:
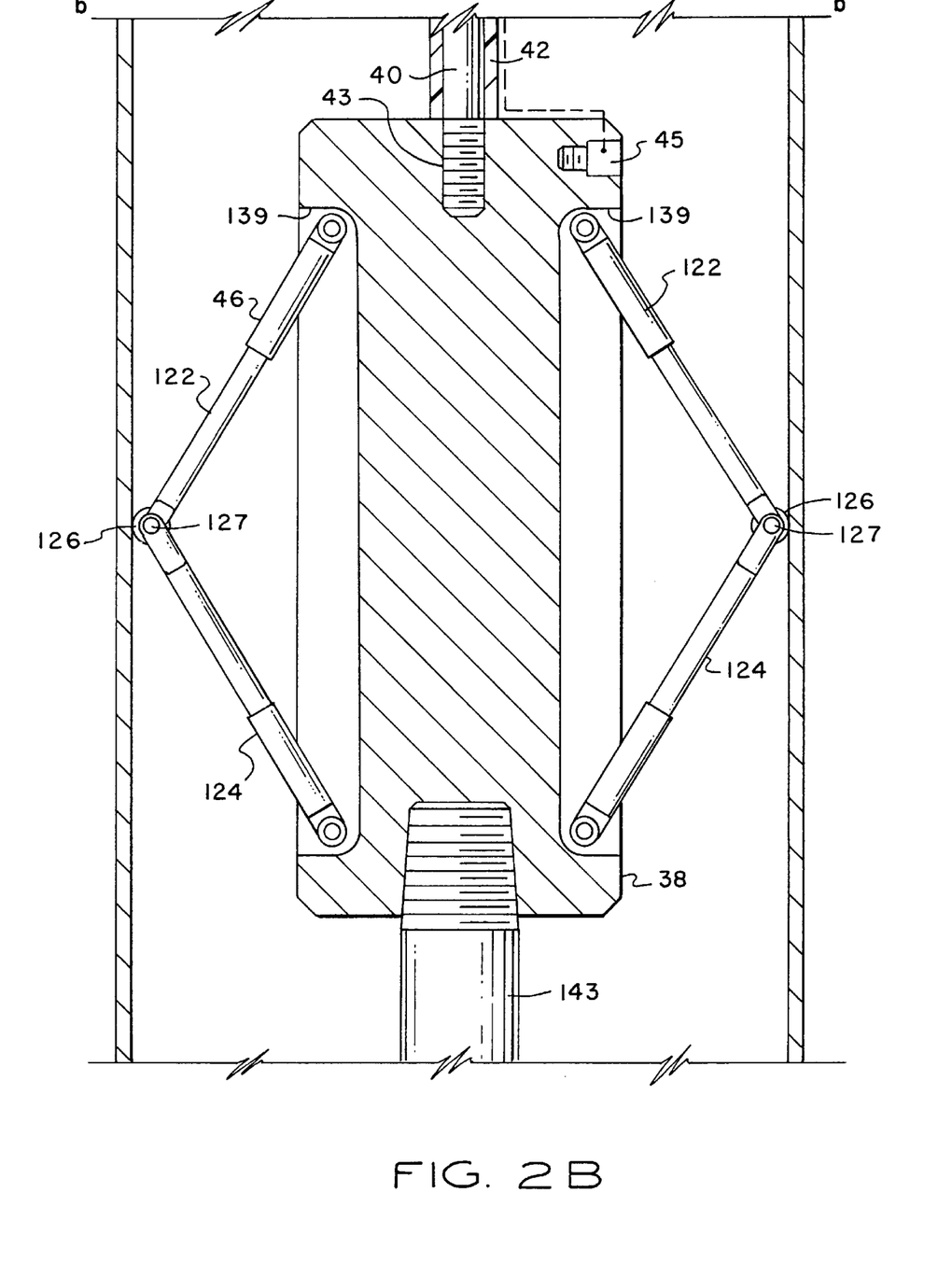

Referring now to FIGS. 2A and 2B, certain details of the downhole apparatus 34 will be described. FIG. 2B is a continuation of FIG. 2A from the lines b—b of the respective figures. The center conductor 40 is electrically isolated from the body member 36 at the end of the center conductor which is connected to the connector 72. The center conductor 40 is connected to a somewhat frusto-conical shaped conductor section 92 which is secured to a third conductor section 94 by a suitable connecting pin 96. The conductor section 94 is also of a somewhat frusto-conical shape and is in engagement with a pin 99 which comprises the center conductor for the connector 72. The pin 99 as well as the conductor sections 94 and 92 are supported in suitable electrical insulating support members 100, 101, and 102 disposed in a bore 103 of the body 36. The center conductor 40 is also suitably isolated from the body 36 by an insulating member 110 disposed in bore 103. The body 36 is adapted to be mechanically connected to the cable 50 by a suitable head member 116 and the cable 50 includes a suitable core passage for receiving conductors 35 and 37. The signal conductors for flowmeter 56, a temperature sensor associated with the apparatus 34 and any other downhole instruments, not shown, supported on or by the apparatus 34, may extend within cable 50, also. In FIG. 2A the aforementioned body extension portion 36a has been omitted and the head 116 is shown directly connected to the body 36.

The body 36 has suitable opposed recesses 39 for receiving opposed sets of centralizer arms 122 and 124 of the centralizer 44. Each set of arms 122 and 124 support a roller 126 rotatably mounted at the distal ends of the arms. Each of the arms 122 and 124 has a suitable support yoke provided thereon for suitable supporting engagement with a pivot pin 127 for the rollers 126. The opposed sets of arms 122 and 124 are operable to bias the rollers 126 into forcible engagement with the casing wall 13 to centralize the apparatus 34 in the space 20 and to provide electrically conductive contact between the body members 36 and 38 and the casing 12. The arms 122 and 124 are each pivotally mounted on the body 36 and are characterized by a sleeve 123 and a rod 125 operably engaged with the sleeve in telescoping relationship. A suitable biasing spring 129 is disposed in each of the sleeves 123 for urging the rods 125 to force the centralizer rollers 126 into engagement with the casing 12.

As will be apparent from viewing FIG. 2B, the body 38 has substantially the same arrangement of centralizer arms 122 and 124 making up the centralizer 46. As shown also in FIG. 2B, the center conductor 40 is threadedly engaged with the body 38 at a distal end 43. The body 38 is made of a suitable highly conductive metal and thus forms a short circuit between the center conductor 40 and the casing 12 through the centralizer 46 including its arms 122, 124 and rollers 126. The rollers 126 form an electrical conductor in contact with casing 12 and are in electrical conductive communication with center conductor 40 through arms 122, 124 and body 38. The centralizer 44 is in electrically conductive engagement with casing 12 and body 36. A suitable temperature sensor 45 is mounted on the body 38 for sensing the temperature of fluid flowing through the space 20. The sensor 45 is operably connected to a suitable signal converter circuit 89, FIG. 1. The body 38 also has opposed recesses 139 for receiving the opposed sets of arms 122 and 124 of centralizer 46 in respective retracted positions to facilitate moving the apparatus 34 through the tubing 22. A connector 143 is secured to the body 38 for supporting the flowmeter 56. FIG. 2A shows one set of arms 122, 124 in a retracted position in a recess 39. The arms of each centralizer 44 and 46 are spring biased to extend into the working positions shown. Other centralizer mechanisms may be used in place of the exemplary centralizers 44 and 46.

Figure 3:
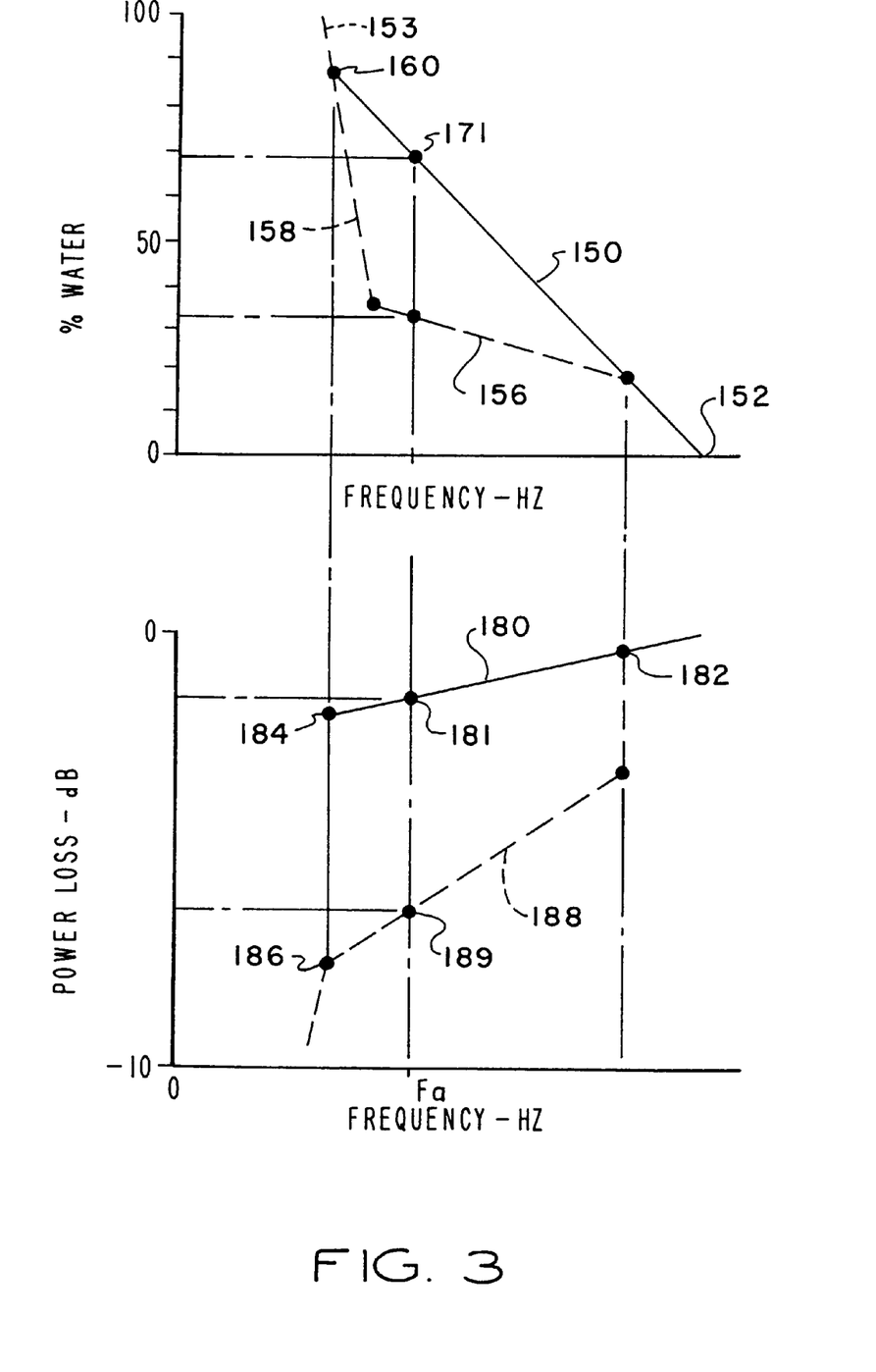
FIG. 3 is a diagram illustrating the change in operating frequency and power loss resulting from the change in concentration of water in a water-oil mixture.

Referring now to FIG. 3, the two diagrams illustrated indicate the characteristics of the change in oscillator operating frequency as a function of the concentration of water in oil, such as crude petroleum. The abscissas of both diagrams of FIG. 3 are not indicated to have any particular numerical values since these representations are intended to be of a somewhat general nature. The frequency of operation of the oscillator 60 as a function of the percentage of water in a water-oil mixture is indicated by the curve or line 150. For example, at a percent of water approximately nil or zero the operating frequency of the oscillator 60 would be indicated by the point 152 and, from experiments, as the volumetric fraction of water in a water-crude petroleum mixture increases to about fifty percent of the total volume, the water exists as an emulsion in an oil liquid. In a range of concentration of from about fifty percent to eighty-six percent water, an inversion may occur wherein the emulsion becomes one of oil in water rather than water in oil. Above eighty-six percent water, almost universally, the emulsion is one of oil-in-water. A slight increase in the slope of the curve 150 occurs over a portion 153 in the range of eighty-six percent to one hundred percent water in the liquid mixture.

It has been observed that, with an increase in the concentration of water in a water-oil mixture, the characteristic of the frequency change is indicated by the curve 150. However, in instances where a relatively high concentration of water in the mixture is initially present but then decreases, and/or wherein an oil-in-water emulsion exists, the change in oscillator operating frequency follows a curve 156 as indicated by the dashed line in the frequency versus percentage of water diagram. This dashed line 156 follows the slope indicated in the diagram to a point wherein the amount of water equals about thirty-six percent by volume of the mixture, then the slope of the curve changes to follow the line 158 to the point where it intersects the curve 150 as indicated at point 160.

As pointed out in U.S. Pat. No. 4,996,490, there is also a change in the microwave radiation power loss through the apparatus 34 as a function of the condition wherein there is either a water-in-oil mixture or an oil-in-water mixture. Looking at the diagram which represents frequency in the abscissa versus microwave power loss in the ordinate, the solid line curve 180 indicates the microwave power loss through the measurement apparatus 34 for a condition of water-in-oil from the point 182 to the points 184, 186. The dashed line 188 in the diagram of frequency versus power loss indicates the power loss for a condition wherein the mixture is essentially an oil-in-water emulsion.

Accordingly, in operation of the system of FIG. 1, including the apparatus 34, the incident power sensed at the power sensor 78, as input to the apparatus 34, may be monitored and the transmitted power as determined by the power sensor 80 may also be monitored. The difference between the readings of these power sensors is then measured to determine the power loss at a particular operating frequency of the circuit 60. At an operating frequency of $F_a$, for example, if the power loss compares or corresponds to the loss indicated by the curve 188 at point 189, it is indicated that an oil-in-water mixture exists. Accordingly, for the same frequency of operation, $F_a$, viewing the diagram of frequency versus percent water, it is indicated that approximately thirty-two percent water is present. On the other hand, for an operating frequency $F_a$, if the power loss compares or corresponds to that indicated by the curve 180 at point 181, it is known that a much higher percentage of water is present in the mixture and corresponding to the percentage of water indicated by the point 171 on line 150 for the same operating frequency $F_a$.

The apparatus 34 may be deployed in a well which is producing fluids from several spaced-apart zones, such as zones 14, 16 and 18 in FIG. 1. The apparatus 34 may be traversed downward until it is measuring the water-oil mixture being produced by zone 18 only and the total flow rate may be simultaneously measured by the flowmeter 56, whose output signal is readable at a suitable signal display and recording device 61, FIG. 1. While transmitting microwave frequency range electromagnetic energy from the oscillator 60 to the apparatus 34, the apparatus may be traversed up through the well by the cable 50 and the change in frequency versus power loss may be continuously monitored to indicate the composition of the fluids flowing through the space 20 on a substantially continuous basis as a function of depth in the wellbore. Wellbore fluid temperature and flow rate may also be monitored. In this way, a zone such as any of the zones 14, 16 or 18 which is producing excessive water may be identified. Upon withdrawal of the apparatus 34 from the well 10 suitable perforation blocking operations may be carried out to isolate the zone which may be contributing excessive water to fluid production from the well.

Thanks to the provision of the apparatus 34, which utilizes the casing 12 as the outer conductor in measuring the alteration of the microwave radiation characteristics a more accurate measurement of the composition of the fluid mixture flowing through the wellbore space 20 may be determined without impeding flow through the well and while also measuring the fluid flow rate using the flowmeter 56. The apparatus 34 may be easily deployed in the well 10 and removed therefrom and may be operated to continuously measure the flow rate as well as the composition of the fluids flowing from the space 20 to the surface through the tubing 22.

Figure 4:
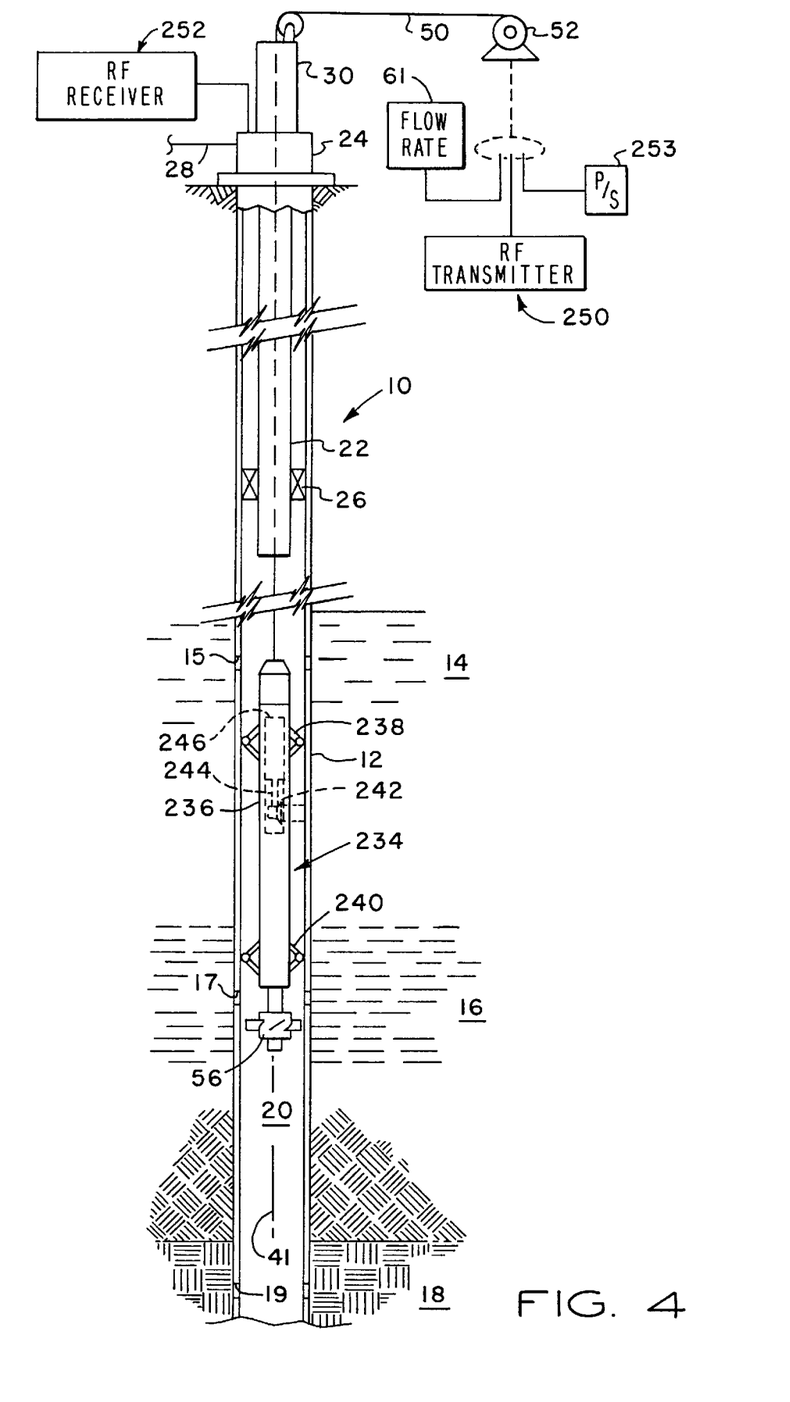
FIG. 4 is a schematic diagram of a first alternate embodiment of the invention.

Referring now to FIG. 4 there is illustrated an arrangement of a first alternate embodiment of a system in accordance with the invention wherein an apparatus 234 is disposed in the well 10 in place of the apparatus 34 and depending from the cable 50 within the casing 12. The apparatus 234 includes an elongated, generally cylindrical body 236 having suitable centralizer devices 238 and 240 disposed thereon for centralizing the apparatus 234 in the wellbore space 20. The flowmeter 56 depends from the lower distal end of the body 236 in a manner similar to the arrangement of the apparatus 34.

The apparatus 234 includes a rotatable RF energy transmitting antenna 242 disposed on the body 236 for transmitting RF energy in the microwave frequency range in a direction generally normal to the wellbore axis 41 and incident on the casing 12. The antenna 242 is preferably mounted for rotation about the wellbore axis on a suitable rotatable shaft 244 which is connected to a suitable drive motor and signal transmission means 246, also disposed in the body 236. The body 236 may be formed, at least in part, of a material which is transparent to the RF energy beam being transmitted from the antenna 242 toward the casing 12. By rotating the antenna 242, a substantially uniform or average signal intensity is received by the casing 12 over a predetermined period of time. The body 236 may also house a suitable RF transmitter operably connected to the antenna 242 or, as shown in FIG. 4, an RF transmitter 250 may be disposed on the surface and operably connected to the antenna 242 by suitable conductor means extending within the cable 50.

In the embodiment of the system illustrated in FIG. 4, the casing 12 acts as a receiving antenna which is suitably connected by way of the wellhead 24 to an RF energy receiver 252. Accordingly, the signal intensity of the RF energy transmitted from the antenna 242 to the receiving antenna comprising the casing 12 may be measured and compared to the transmissivity of a particular signal as a function of the water content of a water-oil mixture flowing within the wellbore space 20. The intensity of the signal received by the RF receiver 252 may be compared with the intensity of the signal emitted by the antenna 242 and with a previously determined range of signal intensities as a function of the composition of the fluid flowing in the wellbore space to determine, in situ, the water content of a water-oil mixture in the wellbore. The apparatus 234 may be traversed through the wellbore space 20 in the same manner as the apparatus 34 and signals may be received during movement of the apparatus or upon the apparatus making brief stops at various points in the wellbore space 20 with respect to the perforations 15, 17 and 19. In this way the system shown in FIG. 4 may be operated to determine what formation zones may be producing excessive amounts of water into the well 10.

Figure 5:
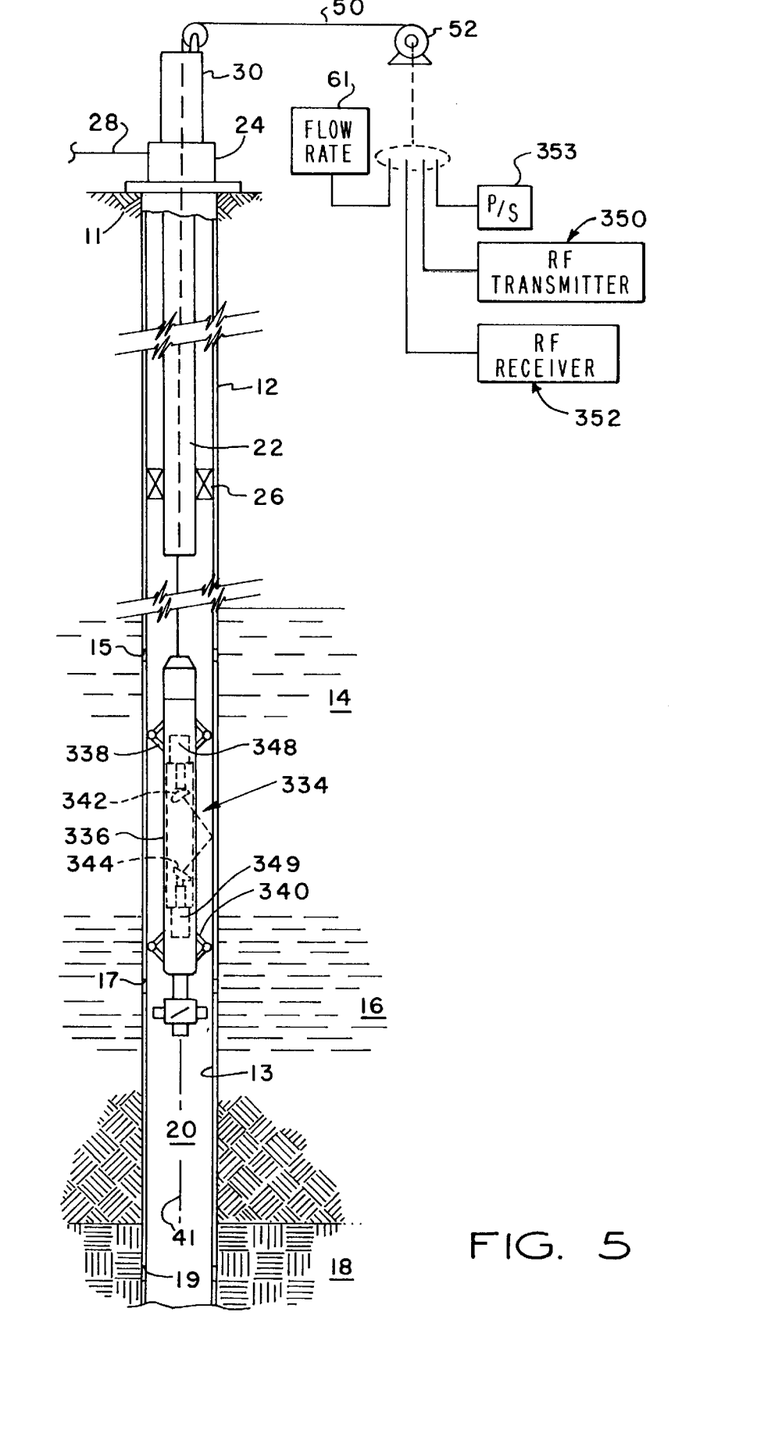
FIG. 5 is a schematic diagram of a second alternate embodiment of the invention.

Referring now to FIG. 5 a second alternate embodiment of a system in accordance with the invention is illustrated being used in conjunction with the well 10 for measuring the water content of a water-oil mixture flowing within the wellbore space 20, preferably toward the production tubing 22. The system illustrated in FIG. 5 includes a downhole apparatus 334 similar in some respects to the apparatus 234 and characterized by an elongated, generally cylindrical body 336 which is centralized in the wellbore space 20 by suitable centralizer devices 338 and 340 spaced apart on the body 336. The apparatus 334 is shown disposed in the wellbore space 20 depending from a modified cable 50 which has suitable conductors therein for conducting signals to the apparatus 334 from an RF transmitter 350. An RF receiver 352 is suitably connected to the device 334 by way of the cable 50. The RF transmitter 350 is operable to transmit an RF signal in the microwave frequency range to a suitable antenna 342 disposed in the body 336 and adapted to transmit an RF signal at a predetermined angle incident to the inside wall surface 13 of the casing 12 for reflection toward a receiving antenna 344 also disposed in the body 336. The body 336 preferably has a hollow portion for accommodating the antennas 342 and 344 and which is made of a suitable material which is substantially transparent to the RF energy being transmitted between the antennas 342 and 344 through the fluid in the wellbore space 20 and reflected by the casing 12. The respective antennas 342 and 344 may be rotated by suitable motor means 348 and 349, respectively, and in synchronization so that the signals transmitted by the antenna 342 and reflected from the casing 12 are received by the antenna 344. By rotating the antennas 342 and 344 a uniform signal change will be sensed by the antenna 344 over a predetermined time period to compensate for any lack of uniformity in the mixture of fluids flowing through the wellbore space 20. Alternatively, the antennas 342 and 344 may be stationary and omnidirectional for transmitting and receiving, respectively, microwave range RF energy.

The intensity of the microwave signal received by the receiver 352 is compared with the transmitted signal and referenced against a predetermined signal intensity scale as a function of the water content of the water-oil mixture in the wellbore space so that the water content can be measured in situ and production of water from one or more of the zones 14, 16 and 18 can be monitored. As with the embodiments described above in conjunction with FIGS. 1 and 4, it may be advantageous to place the signal transmitting and receiving apparatus associated with the system shown in FIG. 5 in the downhole apparatus with only a resultant signal related to the composition of the fluid mixture being transmitted to the surface by way of the cable 50. As shown in FIGS. 4 and 5, power sources 253 and 353 may be disposed at the surface for transmission of suitable electrical power to the apparatus 234 and 334, as needed.

The construction and operation of embodiments of the apparatus described herein is believed to be understandable to those of skill in the art from the foregoing description. Certain components which are commercially available have been described herein. Other well known components which are commercially available and will be recognizable by those of skill in the art have not been specifically identified. Those skilled in the art will also recognize that various substitutions and modifications may be made to the method and apparatus of the invention without departing from the scope and spirit of the appended claims.

What is claimed is:

1. A system for measuring composition of a wellbore fluid flowing through a well, said well including an elongated generally cylindrical metal casing extending within said well for conducting said fluid therethrough, said system comprising:

an apparatus insertable in said casing within said well, said apparatus comprising:

a center conductor extending within said casing; and centralizer means operably connected to said center conductor and engageable with said casing for positioning said center conductor substantially coaxially within said wellbore and with respect to said casing, said centralizer means being engaged with said casing wherein said center conductor and said centralizer means cooperate to form a coaxial transmission line for transmitting RF energy within said well; and a circuit connected to said apparatus including means for indicating a change in at least one characteristic of said RF energy during transmission thereof as a function of a composition property of said fluid.

2. The system set forth in claim 1 wherein:

said apparatus is connected to means for traversing said apparatus through said well to detect a change in said composition property of fluid flowing into said well from at least one earth formation zone as a function of said change in said at least one characteristic of said RF energy.

3. The system set forth in claim 2 wherein:

said system includes means for measuring the volumetric flow rate of fluid flowing within said well and flowing past said apparatus.

4. The system set forth in claim 1 wherein:

said circuit includes an unisolated oscillator operably connected to said apparatus for generating RF energy in a microwave-frequency range and at frequency which changes with a change in a complex impedance of an oscillator load which includes a composition property of said fluid flowing through said well.

5. The system set forth in claim 4 wherein:

said oscillator is a free running voltage controlled oscillator.

6. The system set forth in claim 4 wherein:

said circuit includes means for measuring a power loss of said RF energy transmitted through said apparatus.

7. The system set forth in claim 6 wherein:

said means for measuring power loss includes a first directional coupler interposed between said circuit and said apparatus and a power sensor operably connected to said first directional coupler; and a second directional coupler interposed between said apparatus and said circuit and a power sensor operably connected to said second directional coupler.

8. The system set forth in claim 1 wherein:

said centralizer means includes spaced apart centralizer arms engageable with said casing, at least one of said arms including a member forming an electrical conductor in contact with said casing and in electrical conductive communication with said center conductor.

9. The system set forth in claim 1 wherein:

said fluid flowing through said well is electrically conductive and said apparatus includes a sheath disposed around said center conductor and having a low dielectric loss tangent so as to minimize termination of an electrical field being propagated through said transmission line due to the conductivity of said fluid.

10. The system set forth in claim 9 wherein:

said center conductor and said sheath are cylindrical and an outer diameter of said sheath is about twice as great as an outer diameter of said center conductor.

11. Apparatus for insertion in a well for measurement of at least one composition property of fluid flowing through said well, said apparatus comprising:

an elongated center conductor cooperable with a metal casing of said well to form a coaxial RF energy transmission line;

spaced apart body members connected to and supporting said center conductor in said well;

radially extensible centralizers connected to each of said body members and operable to engage said casing to centralize said center conductor substantially coaxially with respect to said casing in a wellbore space defined by said casing;

a connector connected to one of said body members and to means for traversing said apparatus through said well; and a circuit operably connected to said center conductor for generating microwave frequency range RF energy for transmission through said apparatus and including means for measuring said composition property of said fluid during said transmission by indicating at least one of an operating frequency of said circuit and power loss of said RF energy during said transmission.

12. The apparatus set forth in claim 11 including:

an insulator supporting said center conductor in one of said body members to prevent transmission of microwave energy from said center conductor to said one body member, said center conductor being coupled to said other body member in electrically conductive engagement; and said centralizers each include a contactor engageable with said casing and connected to an electrical conductor extending between said body members and said casing, respectively.

13. The apparatus set forth in claim 11 including:

a flowmeter connected to said apparatus for measuring the flow rate of fluid flowing through said well.

14. The apparatus set forth in claim 11 wherein:

said centralizers each include opposed arms supporting roller means engageable with said casing for supporting said apparatus in said well for traversal through said casing while maintaining said center conductor substantially coaxially disposed in said well with respect to said casing.

15. The apparatus set forth in claim 11 wherein:

said circuit is disposed on a surface of the earth above said well and is operably connected to said center conductor through conductor means associated with a cable for traversing said apparatus in said well.

* * * * *